US012396685B2

(12) United States Patent
Choi et al.

(10) Patent No.: US 12,396,685 B2
(45) Date of Patent: *Aug. 26, 2025

(54) SYSTEMS AND METHODS FOR CARDIOVASCULAR BLOOD FLOW AND MUSCULOSKELETAL MODELING FOR PREDICTING DEVICE FAILURE OR CLINICAL EVENTS

(71) Applicant: HeartFlow, Inc., Redwood City, CA (US)

(72) Inventors: Gilwoo Choi, Mountain View, CA (US); Charles A. Taylor, Atherton, CA (US); Leo J. Grady, Millbrae, CA (US)

(73) Assignee: Heartflow, Inc., Mountain View, CA (US)

( * ) Notice: Subject to any disclaimer, the term of this patent is extended or adjusted under 35 U.S.C. 154(b) by 1409 days.

This patent is subject to a terminal disclaimer.

(21) Appl. No.: 16/898,672

(22) Filed: Jun. 11, 2020

(65) Prior Publication Data

US 2020/0305797 A1 Oct. 1, 2020

Related U.S. Application Data

(63) Continuation of application No. 14/963,743, filed on Dec. 9, 2015, now Pat. No. 10,716,513.

(60) Provisional application No. 62/149,180, filed on Apr. 17, 2015.

(51) Int. Cl.
| | |
|---|---|
| A61B 5/00 | (2006.01) |
| A61B 5/02 | (2006.01) |
| A61B 5/021 | (2006.01) |
| A61B 5/026 | (2006.01) |
| A61B 5/055 | (2006.01) |
| A61B 5/11 | (2006.01) |
| A61B 34/00 | (2016.01) |
| A61B 34/10 | (2016.01) |
| G16H 50/30 | (2018.01) |
| G16H 50/50 | (2018.01) |

(52) U.S. Cl.
CPC .............. *A61B 5/72* (2013.01); *A61B 5/0022* (2013.01); *A61B 5/026* (2013.01); *A61B 5/055* (2013.01); *A61B 5/1118* (2013.01); *A61B 34/00* (2016.02); *A61B 34/10* (2016.02); *G16H 50/30* (2018.01); *G16H 50/50* (2018.01); *A61B 5/02007* (2013.01); *A61B 5/021* (2013.01); *A61B 2034/105* (2016.02); *A61B 2562/0219* (2013.01)

(58) Field of Classification Search
None
See application file for complete search history.

(56) References Cited

U.S. PATENT DOCUMENTS

| 8,315,812 B2 | 11/2012 | Taylor |
| 2011/0060576 A1 | 3/2011 | Sharma et al. |
| 2012/0053918 A1 | 3/2012 | Taylor |
| 2015/0164452 A1 | 6/2015 | Choi et al. |

OTHER PUBLICATIONS

Robertson et al., "Biomechanical Response of Stented Carotid Arteries to Swallowing and Neck Motion", 2008, pp. 663-671, vol. 15, Journal of Endovascular Therapy (9 pages).
Papaharilaou et al., "Effect of Head Posture on the Healthy Human Carotid Bifurcation Hemodynamics", Feb. 2013, pp. 1-30, Medical & Biological Engineering & Computing (30 pages).
Müller et al., "A global multi-scale mathematical model for the human circulation with emphasis on the venous system", Apr. 4, 2013, pp. 1-50, Isaac Newton Institute for Mathematical Sciences, University of Cambridge, UK, reprint (51 pages).
Choi et al., "Methods for Quantifying Three-Dimensional Deformation of Arteries due to Pulsatile and Nonpulsatile Forces: Implications for the Design of Stents and Stent Grafts", Jan. 1, 2009, pp. 14-33, vol. 37, No. 1, Annals of Biomedical Engineering (20 pages).
NíGhriallais et al., "A Computational Analysis of the Deformation of the Femoropopliteal Artery With Stenting", Jul. 2014, vol. 136, Journal of Biomedical Engineering (10 pages).
Rosenfield et al., "Restenosis of Endovascular Stents From Stent Compression", Feb. 1997, pp. 328-338, vol. 29, No. 2, Journal of the American College of Cardiology Foundation (11 pages).
Bohanec M et al.: "Applications of qualitative multi-attribute decision models in health care", International Journal of Medical Informatics, Elsevier Scientific Publishers, Shannon, IR, vol. 58-59, Sep. 1, 2000 (Sep. 1, 2000), pp. 191-205.

(Continued)

*Primary Examiner* — Lori A. Clow
(74) *Attorney, Agent, or Firm* — Bookoff McAndrews, PLLC

(57) ABSTRACT

Computer-implemented methods are disclosed for assessing the effect of musculoskeletal activities on disease and/or clinical events, the method comprising: receiving a patient-specific vascular and musculoskeletal model of a patient's anatomy, including at least one vessel of the patient; receiving at least one characteristic of the patient's musculoskeletal activity; generating or updating a computational anatomic vascular and musculoskeletal model of the patient's anatomy based on the received at least one characteristic of musculoskeletal activity; performing at least one of a computational fluid dynamics analysis or a structural mechanics simulation on the computational anatomic vascular and musculoskeletal model; and estimating at least one of the patient's risk of disease or clinical events based on the performed computational fluid dynamics analysis and/or structural mechanics simulation. Systems and computer readable media for executing these methods are also disclosed.

20 Claims, 5 Drawing Sheets

(56) References Cited

OTHER PUBLICATIONS

Vineeth Nallure Balasubramanian et al.: "Support vector machine based conformal predictors for risk of complications following a coronary drug eluting stent procedure—Arizona State University", Jan. 1, 2009 (Jan. 1, 2009), Retrieved from the Internet: URL:https://asu.Pure.elsevier.com/en/publications/support-vector-machine-based-conformal-predictors-for-risk-of-com [retrieved on Jun. 15, 2016], 4 pages.
International Search Report and Written Opinion for corresponding Application No. PCT/US2016/026149 dated Jul. 4, 2016 (13 pages).
Lyden et al. (Med Sci Sports Exerc (2014) vol. 46(2):386-397).

SYSTEMS AND METHODS FOR CARDIOVASCULAR BLOOD FLOW AND MUSCULOSKELETAL MODELING FOR PREDICTING DEVICE FAILURE OR CLINICAL EVENTS

RELATED APPLICATION(S)

This application is a continuation of and claims the benefit of priority to copending U.S. application Ser. No. 14/963,743, filed Dec. 9, 2015, which claims priority to U.S. Provisional Application No. 62/149,180, filed Apr. 17, 2015, each of which is incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods for assessing the effect of musculoskeletal activities on device failure, arterial diseases, and/or venous diseases, and to guide diagnosis and/or treatment of a patient.

BACKGROUND

Various activities and behaviors of a patient may affect characteristics of the patient's blood flow through the patient's arterial and venous systems. For example, physical activities and sedentary behavior of a patient may affect the geometric configuration of vasculatures, as well as blood flow characteristics therethrough. For example, physical activities, such as walking, running, exercising, swallowing, and head rotation, etc., as well as sedentary behaviors, such as prolonged sitting, may impact the ability of the arterial and venous systems to circulate blood.

In recent studies, individuals with excessive sedentary behavior (e.g., prolonged sitting) were reported to have an increased risk of morbidity and mortality with vascular disease or diabetes, regardless of the intensity of physical activity. To understand the pathogenesis of arterial and venous diseases, a desire exists for accurate modeling of the interaction between musculoskeletal, venous, and arterial systems of a patient and the effects of musculoskeletal activity on the mechanical and/or hemodynamic characteristics of the musculoskeletal and/or vascular systems of a patient. Moreover, this musculoskeletal and vascular modeling may also help assess the durability/lifecycle of implanted endovascular devices, such as stents. This disclosure includes systems and methods for assessing the effect of musculoskeletal motions on device failure, and arterial and venous diseases.

The foregoing general description and the following detailed description are exemplary and explanatory only and are not restrictive of the disclosure.

SUMMARY

According to certain aspects of the present disclosure, systems and methods are disclosed for assessing the effect of musculoskeletal motions on device failure and arterial and venous diseases.

Computer-implemented methods are disclosed for assessing the effect of musculoskeletal activities on disease and/or clinical events, the method comprising: receiving a patient-specific vascular and musculoskeletal model of a patient's anatomy, including at least one vessel of the patient; receiving at least one characteristic of the patient's musculoskeletal activity; generating or updating a computational anatomic vascular and musculoskeletal model of the patient's anatomy based on the received at least one characteristic of musculoskeletal activity; performing at least one of a computational fluid dynamics analysis or a structural mechanics simulation on the computational anatomic vascular and musculoskeletal model; and estimating at least one of the patient's risk of disease or clinical events based on the performed computational fluid dynamics analysis and/or structural mechanics simulation.

In accordance with another embodiment, computer systems are disclosed for assessing the effect of musculoskeletal activities on disease and/or clinical events, the system comprising: a data storage device storing instructions for the determining the effect of musculoskeletal activities in diagnosing or treating disease, or predicating clinical events; and a processor configured to execute the instructions to perform a method including: receiving a patient-specific vascular and musculoskeletal model of a patient's anatomy; generating or updating a computational anatomic vascular and musculoskeletal model of the patient's anatomy based on the received at least one characteristic of musculoskeletal activity; performing at least one of a computational fluid dynamics analysis or a structural mechanics simulation on the computational anatomic vascular and musculoskeletal model; and estimating at least one of the patient's risk of disease or clinical events based on the performed computational fluid dynamics analysis and/or structural mechanics simulation.

In accordance with another embodiment, non-transitory computer readable media are disclosed for use on a computer system containing computer-executable programming instructions for performing a method of assessing the effect of musculoskeletal activities on disease and/or clinical events, the method comprising: receiving a patient-specific vascular and musculoskeletal model of a patient's anatomy, including at least one vessel of the patient; receiving at least one characteristic of the patient's musculoskeletal activity; generating or updating a computational anatomic vascular and musculoskeletal model of the patient's anatomy based on the received at least one characteristic of musculoskeletal activity; performing at least one of a computational fluid dynamics analysis or a structural mechanics simulation on the computational anatomic model vascular and musculoskeletal; and estimating at least one of the patient's risk of disease or clinical events based on the performed computational fluid dynamics analysis and/or structural mechanics simulation.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The following description includes exemplary non-invasive methods for modeling musculoskeletal motions. In one embodiment, the modeled musculoskeletal motions may provide an estimated risk to predict device failure, and arterial and venous diseases. In one embodiment, such a risk may be used to evaluate therapeutic options.

Figure 1:
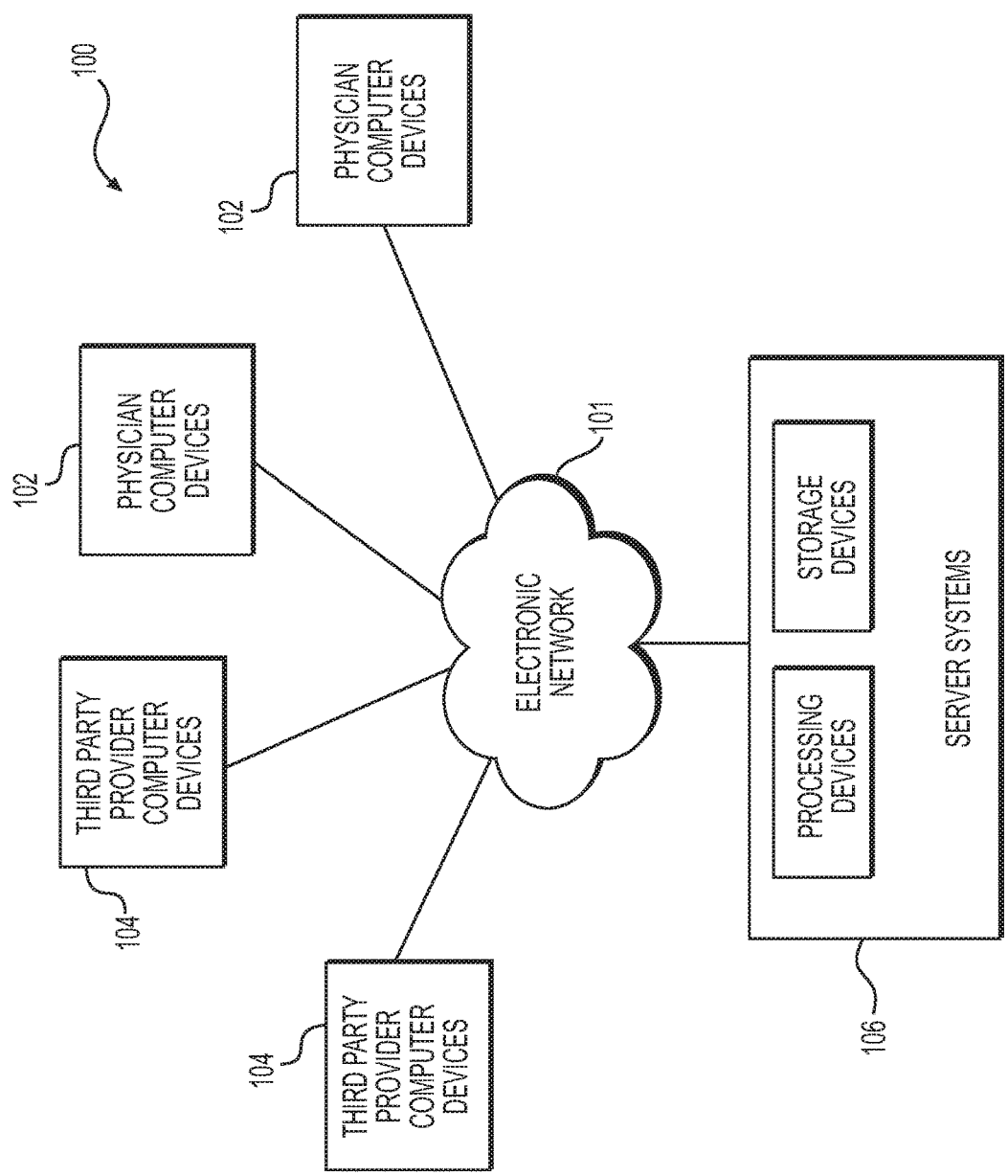
FIG. 1 is a block diagram of an exemplary system and network for assessing the effects of musculoskeletal activities on device failure, and arterial and venous diseases.

Referring now to the figures, FIG. 1 depicts a block diagram of an exemplary system 100 and network for assessing the effects of musculoskeletal motions on device failure, and arterial and venous diseases, according to an exemplary embodiment. Specifically, FIG. 1 depicts a plurality of physician computer devices 102 and third party provider computer devices 104, any of which may be connected to an electronic network 101, such as the Internet, through one or more computers, servers, and/or handheld mobile devices. Physician computer devices 102 and/or third party provider computer devices 104 may create or otherwise obtain images of one or more patients' anatomy. The physician computer devices 102 and/or third party provider computer devices 104 may also obtain any combination of patient-specific information, such as age, medical history, blood pressure, blood viscosity, patient activity or exercise level, etc. Physician computer devices 102 and/or third party provider computer devices 104 may transmit the anatomical images and/or patient-specific information to server systems 106 over the electronic network 101. Server systems 106 may include storage devices for storing images and data received from physician computer devices 102 and/or third party provider computer devices 104. Server systems 106 may also include processing devices for processing images and data stored in the storage devices.

Figure 2A:
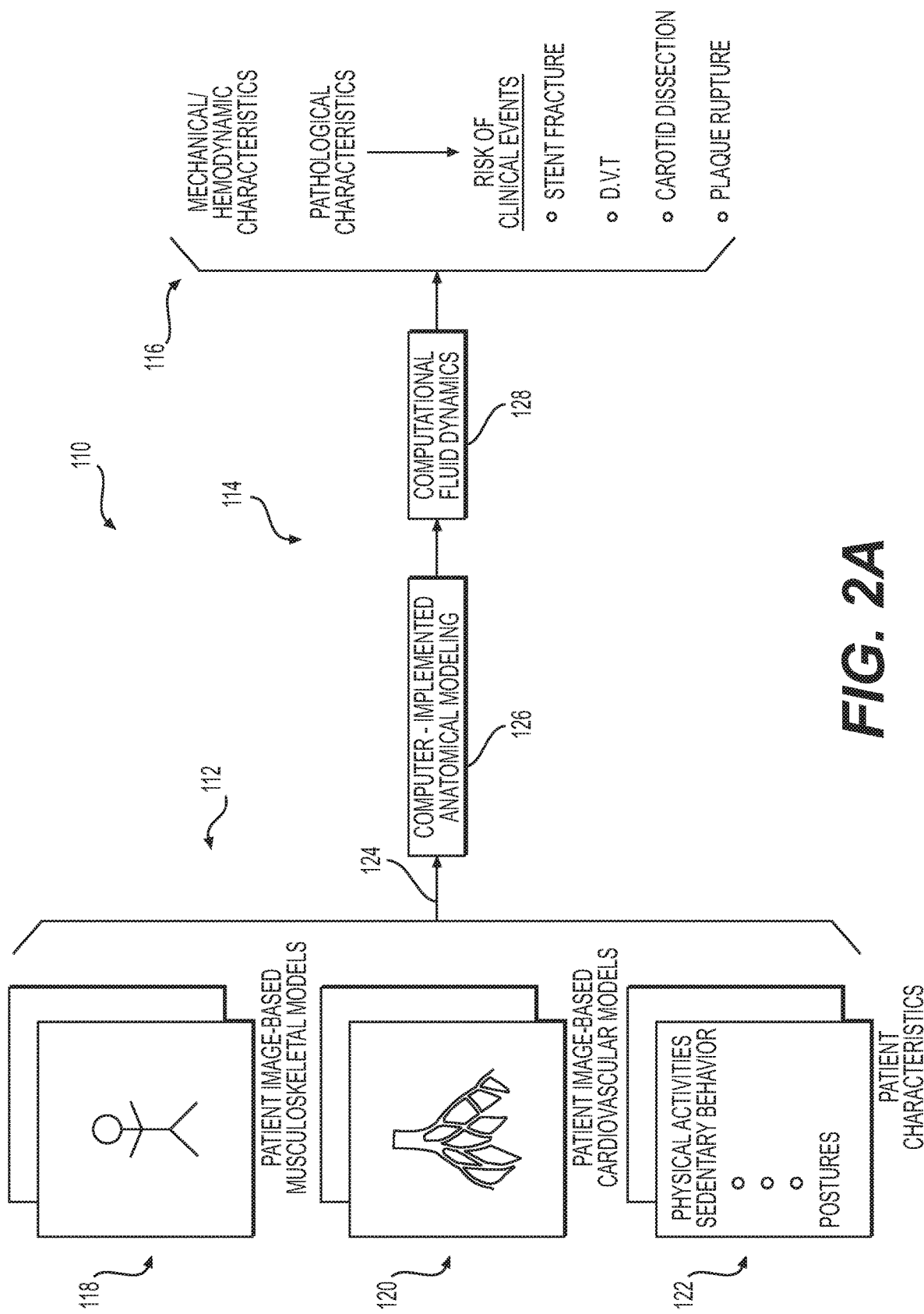
FIG. 2A is a diagram of an exemplary overview of a framework for assessing the effects of musculoskeletal activities on device failure, and arterial and venous diseases, according to an exemplary embodiment of the present disclosure

FIG. 2A is an overview diagram of a system 110 for assessing the effects of musculoskeletal activities on device failure, and arterial and venous diseases, according to an exemplary embodiment of the present disclosure. In one embodiment, the system may include a modeling phase 112, an analysis phase 114, and a prediction phase 116. In general, the modeling phase 112 may involve receiving patient-specific images of one or more systems of a patient's body. Such images may include images from any known medical imaging modality (e.g., CT, MR, SPECT, angiography, etc.). For example, the modeling phase 112 may include receiving images of a specific patient's musculoskeletal system and/or cardiovascular system. Upon receiving such images, a patient image-based musculoskeletal model 118 and/or a patient image-based cardiovascular model 120 may be generated and stored in an electronic storage medium of the server systems 106. In one embodiment, all of the images obtained may be obtained from the same patient or individual. In other embodiments, however, the images obtained may be obtained from multiple patients and/or individuals. Further, the modeling phase may also include receiving one or more patient characteristics 122 in an electric storage medium of server systems 106. These characteristics may include, for example, physical activities performed by a patient as well as sedentary behaviors of the patient and/or postures of the patient, and may be observed over any appropriate length of time such as, for example a day, a week, etc.

Following collection and/or storage of any patient image-based musculoskeletal model 118, patient image-based cardiovascular model 120, and patient characteristics 122, an output 124 may be used as an input to an exemplary analysis phase 114 in which a computational anatomic model, such as computer-implemented anatomical model 126 of the musculoskeletal and vascular systems of the patient may be generated. That is, updated and/or new anatomic model(s) of the patient may be generated based on postural changes reflected by the state (e.g., standing, sitting, lying down) of the patient, the effect of a patient's duration and type of musculoskeletal activities, and/or patient-specific features (e.g., weight, measurements, etc.) on vessel geometry (e.g., collapse of a vessel) and/or musculoskeletal compression. Following generation of the computer-implemented anatomical model 126, computational fluid dynamics analysis 128 and/or structural mechanics simulation may be performed on the computer-implemented anatomical model 126 in conjunction with various determined boundary conditions corresponding to one or more physiological states for blood flow of the arterial or venous system of the patient. Such states may include, for example, reduced blood flow to the lower extremities while the patient is in the seated position, and/or radial pulsatile forces acting on a device (e.g., a stent) within the arterial and/or venous system of the patient.

The results of the computational fluid dynamics analysis 128 and/or structural mechanics simulation may be used as an input to an exemplary prediction phase 116 in which the effect of musculoskeletal activities on the mechanical, hemodynamic, and/or pathological characteristics of the musculoskeletal and/or vascular systems of a patient may be assessed. Such clinical events may include, for example, stent fracture, dissection, plaque rupture, deep vein thrombosis, embolization, etc.

Figure 2B:
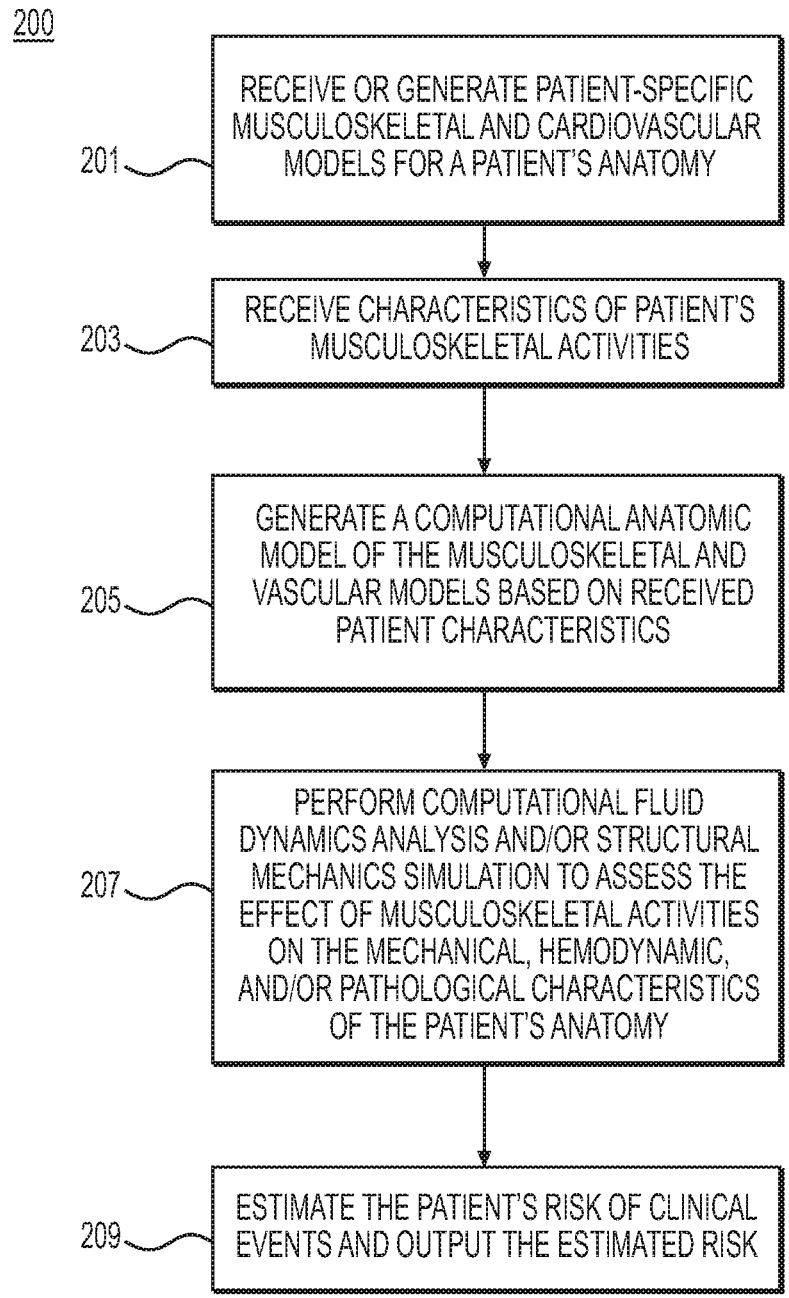
FIG. 2B is a block diagram of an exemplary method of assessing the effects of musculoskeletal activities on device failure, and arterial and venous diseases, according to an exemplary embodiment of the present disclosure.
Figure 3A:
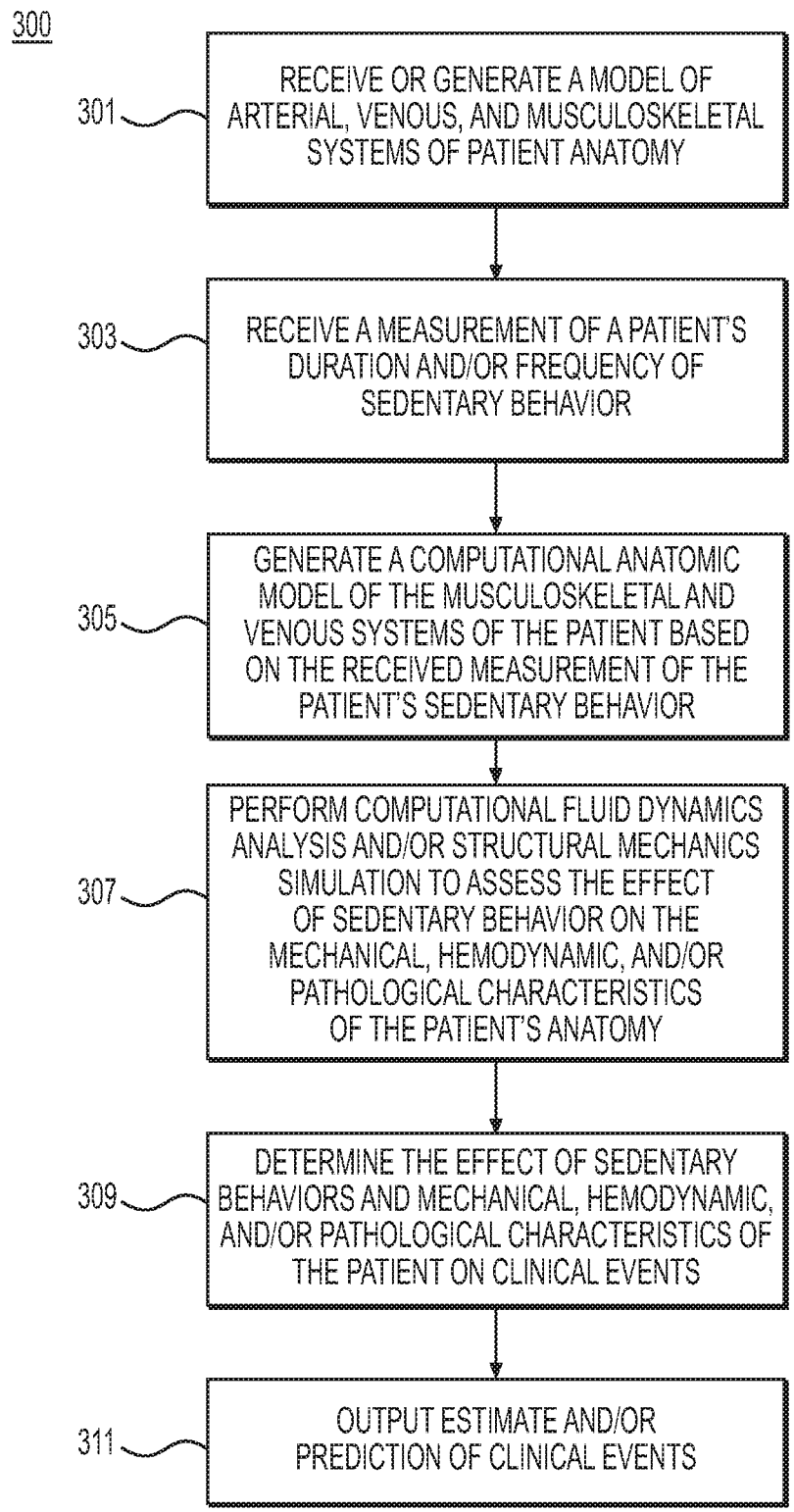
FIG. 3A is a block diagram of an exemplary process of assessing the risk of venous disease by modeling venous flow, arterial flow, and musculoskeletal motion, according to an exemplary embodiment of the present disclosure.
Figure 3B:
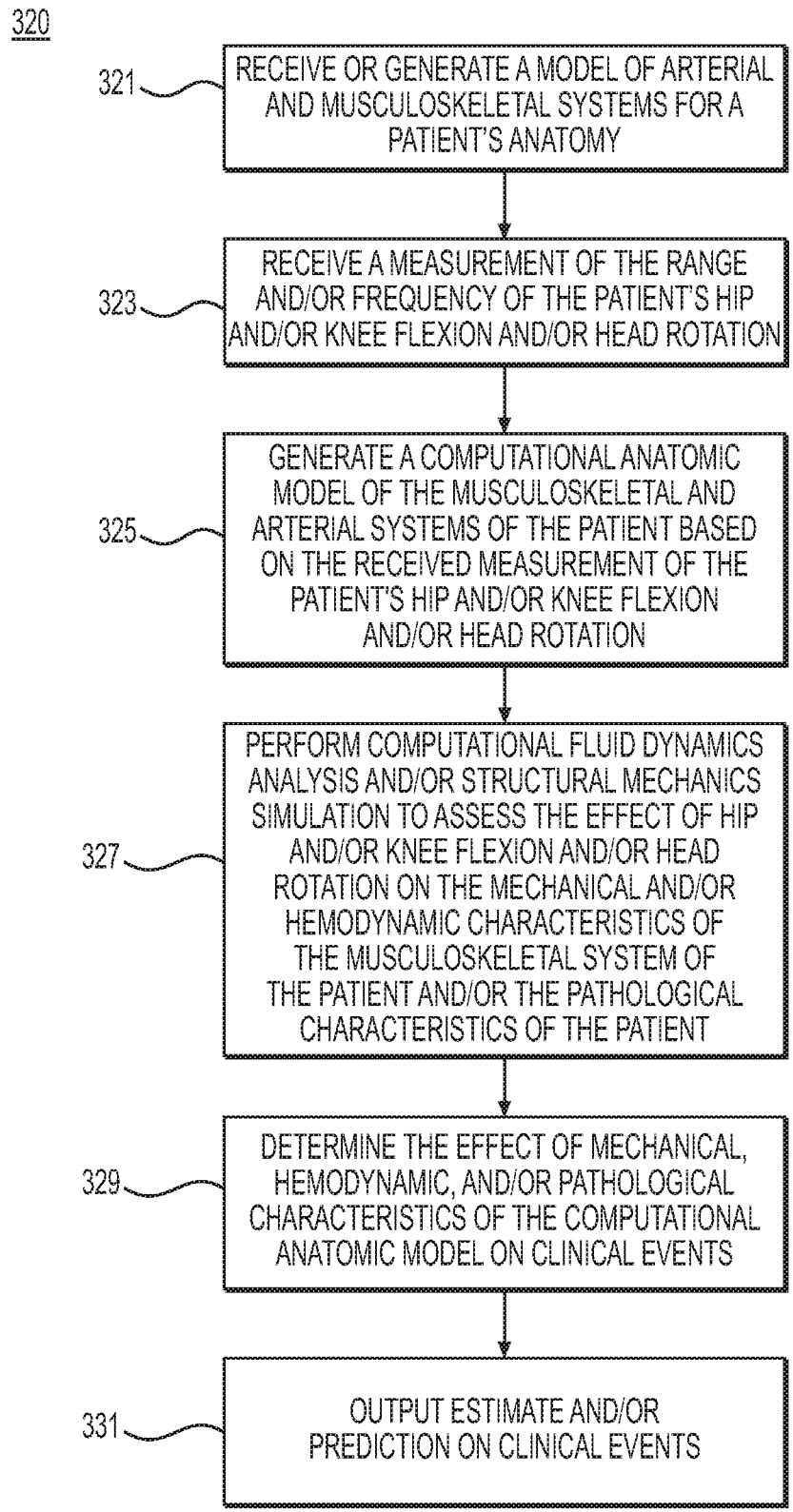
FIG. 3B is a block diagram of an exemplary process of assessing the risk of stent fracture, dissection, and/or plaque rupture by modeling vascular and musculoskeletal interaction, according to an exemplary embodiment of the present disclosure.

FIG. 2B depicts a general embodiment of a method for assessing the effects of musculoskeletal motions on device failure, and arterial and venous diseases. FIGS. 3A and 3B depict exemplary embodiments of the method of FIG. 2B. For example, FIG. 3A depicts an embodiment of a process of assessing the risk of venous disease by modeling venous flow and musculoskeletal motion. FIG. 3B depicts an embodiment of a process of assessing the risk of stent fracture, dissection, and/or plaque rupture by modeling vascular and musculoskeletal interaction.

FIG. 2B is a block diagram of an exemplary method 200 for assessing the effects of musculoskeletal motions on device failure, and arterial and venous diseases, according to an exemplary embodiment. The method of FIG. 2B may be performed by server systems 106, based on information, images, and data received from physicians 102 and/or third party providers 104 over electronic network 101.

In one embodiment, step 201 may include receiving a patient-specific anatomic model in an electronic storage medium of the server systems 106. Specifically, receiving the patient-specific anatomic model may include either generating the patient-specific anatomic model at the server system 106, or receiving one over an electronic network (e.g., electronic network 101). The patient-specific anatomic model may include musculoskeletal and vascular models of a specific person. In one embodiment, the anatomic model may be derived from images of the person acquired via one or more available imaging or scanning modalities (e.g., computed tomography (CT) scans, angiography, and/or magnetic resonance imaging (MRI)) and may include a 3D mesh model or a 1D reduced order model. For example, step 201 may include receiving CT and/or MRI images of one or more portions of a patient's body (e.g., heart, head, etc.) and/or the entirety of a patient's body. Step 201 may further include generating, from the received images, a patient-specific model for the particular person. For the purposes of the disclosure, "patient" may refer to any individual or person for whom diagnosis or treatment analysis is being performed, or any individual or person associated with the diagnosis or treatment analysis of one or more individuals.

In one embodiment, step 203 may include receiving a patient's characteristics of musculoskeletal activities in an electric storage medium of server systems 106. These characteristics may include, for example, physical activities performed by a patient, as well as sedentary behaviors of the patient, and may be observed over any appropriate length of time such as, for example a day, a week, etc. Such physical activities may include, for example, frequencies of waking, swallowing, and head rotation, etc. Sedentary behaviors of a patient may include, for example, sitting (e.g., while working, on a flight, while in a vehicle, etc.) and/or lying down postures (excluding sleeping). These activities and behaviors of a patient may be assessed in any appropriate manner, such as, for example, a wearable device (e.g., pedometers, smart watches, and/or built in capabilities of smart phone sensors) and/or patient survey.

In one embodiment, step 205 may include generating a computational anatomic model of the musculoskeletal and vascular systems of the patient based on the received characteristics of musculoskeletal activities of step 203. That is, step 205 may include determining an updated and/or new anatomic model of the patient based on postural changes reflected by the state (e.g., standing, sitting, lying down) of the patient. For example, step 205 may include determining the effect of a patient's duration and type of musculoskeletal activities, and patient-specific features (e.g., weight, measurements, etc.) on vessel geometry (e.g., collapse of a vessel) and/or musculoskeletal compression.

In one embodiment, step 207 may include performing computational fluid dynamics analysis and/or structural mechanics simulation. This analysis may be performed on the computational anatomic model of the musculoskeletal and vascular systems of the patient in conjunction with various determined boundary conditions corresponding to one or more physiological states for blood flow of the arterial or venous system of the patient. Such states may include, for example, reduced blood flow to the lower extremities while the patient is in the seated position, and/or radial pulsatile forces acting on a device (e.g., a stent) within the arterial and/or venous system of the patient. The results of the computational fluid dynamics analysis and/or structural mechanics simulation may be used to assess the effect of musculoskeletal activities on the mechanical and/or hemodynamic characteristics of the musculoskeletal and/or vascular systems of a patient. Such analyses may also be performed to assess the effect of the musculoskeletal activities on pathological characteristics of a patient.

In one embodiment, step 209 may include estimating the patient risk of clinical events via a computing processor, and outputting the estimated risk to an electronic storage medium and/or a display for use by one or more healthcare providers. Such clinical events may include, for example, stent fracture, dissection, plaque rupture, deep vein thrombosis, embolization, etc. This estimation may be based on the one or more observed patient characteristics of musculoskeletal activities (e.g., physical activities and sedentary behavior) and one or more of a computed mechanical and/or hemodynamic and/or pathological characteristics of the musculoskeletal and/or vascular systems of the patient.

FIG. 3A is a block diagram of an exemplary method 300 of assessing the risk of venous disease by modeling venous flow, arterial flow, and musculoskeletal motion, according to an exemplary embodiment of the present disclosure, according to an exemplary embodiment. The method of FIG. 3A may be performed by server systems 106, based on information, images, and data received from physicians 102 and/or third party providers 104 over electronic network 101.

Blood flow simulation may provide a mechanism for performing a non-invasive assessment of the risk of venous disease (e.g., renal vein thrombosis, deep vein thrombosis, superficial venous thrombosis, and/or embolism, etc.). Relative to arteries, veins may be unique in structure and physiologic condition. For example, veins may be more flexible than arteries, and may additionally include valves controlling the direction of flow during muscle contraction. Accordingly, accurate modeling of venous flow may require analysis of vessel collapse or external pressure on a vessel due to muscle contraction and/or respiration, gravitation effect, and/or venous tone regulation. Determining the effects of musculoskeletal motion on the venous system may provide a means to improve the accuracy of a blood flow simulation by using a patient-specific estimate of vessel structure and condition at various physiological states.

In one embodiment, step 301 may include receiving or generating (e.g., from CT, angiography, and/or MRI images) a model of arterial, venous, and musculoskeletal systems of a patient. Examples of an arterial and/or venous model may include a 3D mesh model and/or a 1D reduced order model. This model may be patient-specific and obtained, e.g., via segmentation of a cardiac, abdominal, or peripheral CT image of the patient. Further, the venous system may be imaged with a delayed scan so as to allow, for example, time for completion of systematic circulation following arterial system acquisition after contrast injection. Examples of a musculoskeletal model may include a 3D volumetric mesh model and/or a 2D surface mesh model. This model may be patient-specific and obtained, e.g., via segmentation of a peripheral CT image or MRI of the patient. Alternatively, the musculoskeletal model may be a generic model based on population averages. Step 301 may further include storing the model in an electronic storage medium of server systems 106.

In one embodiment, step 303 may include receiving a measurement of a patient's duration and/or frequency of sedentary behavior in an electric storage medium of server systems 106. These behaviors may be observed over any appropriate length of time such as, for example a day, a week, etc. Such behaviors of a patient may include a group of behaviors that occur while a patient is sitting or lying down (excluding sleeping) that require very low energy consumption. By way of example only, such behaviors may include sitting or lying while reading a book, while at work or school, while watching television, while using a computer or playing video games, while socializing, while in a car or other form of motorized transport, and/or while on a flight. The sedentary behaviors of a patient may be assessed in any appropriate manner, such as, for example, a wearable device (e.g., pedometers, accelerometers, smart watches, and/or built in capabilities of smart phone sensors). In some cases, the sedentary behavior data may be received in the form of raw accelerometer data, etc., or as parameterized movement/behavior data, and/or as structured/standardized movement/behavior data.

In one embodiment, step 305 may include generating a computational anatomic model of the musculoskeletal and venous systems of the patient based on the received measurement of the patient's sedentary behavior of step 303. That is, step 305 may include determining an updated and/or new anatomic model of the patient based on postural changes reflected by the state (e.g., standing, sitting, and/or lying down) of the patient. For example, step 305 may include determining the effect of a patient's duration and type of sedentary behavior and patient-specific features (e.g., weight, measurements, etc.) on vessel geometry (e.g., collapse of a vessel). The computational anatomic model may be generated via computational structural mechanics simulation and/or by imaging a patient's venous system in various postures (e.g., standing, sitting, and/or lying down) while the patient is positioned in an open MRI.

In one embodiment, step 307 may include performing computational fluid dynamics analysis and/or structural mechanics simulation. This analysis may be performed on the computational anatomic model of the musculoskeletal and venous systems of the patient in conjunction with various determined boundary conditions corresponding to one or more physiological states for blood flow of the arterial and/or venous system of the patient. Such states may include, for example, reduced blood flow to the lower extremities while the patient is in the seated position. The computational fluid dynamic analysis may be used to analyze venous flow characteristics for a normal vein (e.g., an uncompressed vein) and a vein collapsed, compressed, or otherwise narrowed due to patient sedentary behavior (e.g., sitting). Such venous flow characteristics may include, for example, wall shear stress, flow rate, particle residence time, etc. The results of the computational fluid dynamics analysis and/or structural mechanics simulation may be used to assess the effect of sedentary behavior on the mechanical and/or hemodynamic characteristics of the musculoskeletal and/or vascular systems of a patient. Such analyses may also be performed to assess the effect of the musculoskeletal activities on pathological characteristics of a patient.

In one embodiment, step 309 may include determining the effect of sedentary behaviors and mechanical, hemodynamic, and/or pathological characteristics of a patient on clinical events. For example, step 309 may include determining the relationship between particle residence time and deep vein thrombosis and/or embolization. Accordingly, a machine (e.g., a processor) having learned algorithms stored thereon may be employed to determine the effect of sedentary behaviors and mechanical, hemodynamic, and/or pathological characteristics of a patient on clinical events. That is, the machine may execute one or more of the learned algorithms, which may be based on experimental measurements and literature.

For example, step 309 may comprise a first training phase, and a second prediction phase. The training phase may include creating a feature vector for healthy patient groups and venous disease patients (e.g., post-thrombotic and/or post-embolism patients). An exemplary feature vector may include the age, sex, heart rate, systolic and diastolic pressure, and/or epicardial fat (adipose) volume, etc. of healthy patient groups and venous disease patients. The feature vector may also include the myocardial mass, regional density of the myocardium, ejection fraction, and/or myocardial contraction contractility, etc. of healthy patient groups and venous disease patients. Further, the feature vector may include the intensity of sedentary behaviors. For example, the feature vector may include the hours, or portions thereof, of one or more of the following behaviors per period of time (e.g., per day, month, year, etc.): sitting while reading a book, sitting while at work or school, sitting while watching television, sitting while using a computer or playing video games, sitting while socializing, sitting while in a car or other form of motorized transport, sitting while on a flight, etc. It is understood that these behaviors are merely exemplary only, and additional or different behaviors may be included in the feature vector.

Additionally, the feature vector may include hemodynamic and biomechanical characteristics of a vein(s) of healthy patient groups and venous disease patients. Such hemodynamic characteristics may include the duration and maximum velocity of retrograde flow (e.g., venous reflux) in lower extremity veins. The duration and maximum velocity of retrograde flow may be determined by computational fluid dynamics analysis and/or measurements using a duplex ultrasound scanner. Additionally, the hemodynamic characteristics may include particle residence time in veins, which may also be determined via computational fluid dynamics analysis. Biomechanical characteristics of a vein(s) may include distensibility of veins (e.g., femoral, jugular vein) in supine and standing positions. These biomechanical characteristics may be measured by ultrasound.

The training phase may further include associating one or more variables of the patient's characteristics of sedentary behavior as determined in step 303, and the patient's computed mechanical/hemodynamic characteristics as determined in steps 305 and 307 with a clinical representation of healthy patient groups and venous disease patients (e.g., post-thrombotic and/or post-embolism patients) and storing the relationship electronically (e.g., via an electronic storage medium, RAM, etc.). For example, this relationship may be stored in an electronic storage medium of the server systems 106. Further, the training phase may include training a machine learning algorithm (e.g., a linear Support Vector Machine) to analyze and recognize patterns of clinical events from the feature vectors obtained, as described above. Additionally, the training phase may comprise saving the results of the machine learning algorithm as a digital representation. This digital representation may be a memory or digital storage (e.g., a hard drive and/or network drive) of a computational device such as a computer, laptop, DSP, server, etc.

The prediction phase of step 309 may include creating a feature vector of a patient's sedentary behavioral characteristics and hemodynamic characteristics. The feature vector may have the same values and/or quantities as those used in the training phase, as discussed above. Additionally, using the saved results of the machine learning algorithm produced in the training phase (e.g., feature weights), the prediction phase may include producing estimates and/or predictions of the probability of clinical events. These estimates and/or predictions may be produced by the same machine learning technique used in the training phase, described above. Additionally, these estimates and/or predictions of clinical events may be saved to a digital representation or digital storage (e.g., a hard drive and/or network drive) of a computational device such as a computer, laptop, DSP, server, etc. In one embodiment, step 311 may include outputting, e.g., to an electronic storage medium, the estimates and/or predictions of step 309 for use by one or more healthcare providers.

FIG. 3B depicts a block diagram of an exemplary method 320 for assessing the risk of stent fracture, dissection, and/or plaque rupture by modeling vascular and musculoskeletal interaction. The method of FIG. 3B may be performed by server systems 106, based on information, images, and data received from physicians 102 and/or third party providers 104 over electronic network 101.

Stents may be used throughout the arterial system of a patient to treat narrowed or weakened areas in the body. Such stents may be located, by way of example only, within peripheral arteries, coronary arteries, carotid arteries, and the superficial femoral artery. Depending on the location of the stent within the arterial system of the patient, various forces may act on the stent, reducing its lifecycle and/or performance. Such forces may include biomechanical forces due to musculoskeletal and respiratory motions, cardiac pulsatility, swallowing, and head rotation. Stent fracture, often linked to undesirable clinical events, may be reduced by accurate modeling of interaction between musculoskeletal and arterial systems of a patient, with improved endovascular device design. Accordingly, patient-specific modeling of musculoskeletal and arterial systems of a patient may provide a means to improve the prediction of stent and/or endovascular device lifecycles. In other words, the systems and methods disclosed herein may include predicting the risk of stent fracture, dissection, or plaque rupture by patient-specific modeling of arterial and musculoskeletal system interaction. Further, the systems and methods disclosed herein may estimate the lifecycle of implanted stents to ensure device performance (e.g., fracture, drug kinetics of drug-eluting stents, and degradation rates of bioabsorbable stents). Such estimates may aid development of fracture-resistant stents and expedite bench-testing.

In one embodiment, step 321 may include receiving or generating (e.g., from CT and/or MRI images) a model of arterial and musculoskeletal systems of a patient. Examples of an arterial model may include a 3D volumetric mesh model and/or a 2D surface mesh model. This model may be patient-specific and obtained, e.g., via segmentation of a cardiac, abdominal, or peripheral CT and/or MRI image of the patient. Examples of a musculoskeletal model may include a 3D volumetric mesh model and/or a 2D surface mesh model. This model may be patient-specific and obtained, e.g., via segmentation of a peripheral CT image or MRI of the patient. Alternatively, the musculoskeletal model may be a generic model based on population averages. Step 321 may further include storing the model in an electronic storage medium of server systems 106.

In one embodiment, step 323 may include receiving a measurement of various characteristics pertaining to the range and/or frequency of a patient's hip and knee flexion and/or head rotation in an electronic storage medium of server systems 106. These characteristics may be observed over any appropriate length of time, for example, a day, a week, etc. These characteristics may be assessed in any appropriate manner, such as, for example, a wearable device (e.g., pedometers, smart watches, and/or built in capabilities of smart phone sensors). Such characteristics may include, for example, a patient's number of steps per day, hip and knee flexion angle in walking, hip and knee flexion angle in running or exercising, frequency of head rotation, maximum range of head rotation angle, and frequency of swallowing. Additionally, step 323 may include performing patient-specific gait analysis (e.g., evaluate number of steps/day, hip/knee flexion angle, exercise strength, and/or postures (sitting, squatting, etc.)) and finite element analysis. Such analyses may assess fatigue on implanted stents in patient-specific geometry for predicting stent lifecycle.

In one embodiment, step 325 may include generating a computational anatomic model of the musculoskeletal and arterial systems of the patient based on the received measurement of the characteristics pertaining to the range and/or frequency of a patient's hip and knee flexion and/or head rotation of step 323. That is, step 325 may include determining an updated and/or new anatomic model of the patient based on postural changes reflected by the state (e.g., standing, sitting, and/or lying down) of the patient. For example, step 325 may include determining the effect of a patient's hip and knee flexion, swallowing, and/or head rotation on vessel geometry (e.g., collapse of a vessel) and muscular compression. The computational anatomic model may be generated via computational structural mechanics simulation and/or by imaging a patient's arterial system and/or muscles in various postures (e.g., standing, sitting, hip or knee flexing, and/or lying down) while the patient is positioned in an open MRI.

In one embodiment, step 327 may include performing computational fluid dynamics analysis and/or structural mechanics simulation. The results of the computational fluid dynamics analysis and/or structural mechanics simulation may be used to assess the effect of hip and knee flexion and/or head rotation on the mechanical and/or hemodynamic characteristics of the musculoskeletal and/or vascular systems of a patient. Such analyses may also be performed to assess the effect of hip and knee flexion and/or head rotation on pathological characteristics of a patient.

The analysis of step 327 may be performed on the computational anatomic model of the musculoskeletal and arterial systems of the patient in conjunction with various determined boundary conditions corresponding to one or more physiological states for blood flow of the arterial and/or venous systems of the patient. Such states may include, for example, pulsatile flow in the arterial or venous system (e.g., radial pulsatile forces acting on the stent). The computational fluid dynamic analysis and/or structural mechanics simulation (e.g., solid dynamics) may be used to analyze flow and vessel wall dynamics for different vessel configurations according to kinematic ranges of musculoskeletal motions. Performing the computational fluid dynamic analysis and/or structural mechanics simulations may include computation of various flow characteristics such as, for example, pulsatile pressure, wall shear stress, particle residence time, etc. Additionally, performing the computational fluid dynamic analysis and/or structural mechanics simulations may include computation of pulsatile forces acting on the stent (or other endovascular device), due to the fluid pressure and mechanical forces (e.g., radial compression, bending, torsion, axial tension/compression, etc.) acting on the stent due to repeat musculoskeletal motions (e.g., arising from head rotation, swallowing, walking, running, and/or exercising).

In one embodiment, step 329 may include determining the effect of mechanical, hemodynamic, and/or pathological characteristics of the computational anatomic model on clinical events, such as, for example, stent fractures, dissection, plaque rupture, etc. Accordingly, a machine (e.g., a processor) having learned algorithms stored thereon may be employed to determine the effect of mechanical, hemodynamic, and/or pathological characteristics of the computational anatomic model on clinical events. That is, the machine may execute one or more of the learned algorithms, which may be based on experimental measurements and literature.

For example, step 329 may comprise a first training phase, and a second prediction phase. The training phase may include creating a feature vector for patients with stents but without suffering any known prior clinical events (healthy patient), and patients with stents having suffered a known prior clinical event (clinical event patients). An exemplary feature vector may include the age, sex, heart rate, systolic and diastolic pressure, and/or epicardial fat (adipose) volume, etc. of healthy patients and clinical event patients. The feature vector may also include the myocardial mass, regional density of the myocardium, ejection fraction, and/or myocardial contraction contractility, etc. of healthy patients and clinical event patients. Further, the feature vector may include the intensity of sedentary behaviors. For example, the feature vector may include the hours, or portions thereof, of one or more of the following behaviors per period of time (e.g., per day, month, year, etc.): sitting while reading a book, sitting while at work or school, sitting while watching television, sitting while using a computer or playing video games, sitting while socializing, sitting while in a car or other form of motorized transport, sitting while on a flight, etc. It is understood that these behaviors are merely exemplary only, and additional or different behaviors may be included in the feature vector.

Additionally, the feature vector may also or alternatively include the intensity of physical activities. For example, the feature vector may include the hours, or portions thereof, of one or more of the following behaviors per period of time (e.g., per day, month, year, etc.): number of steps, hip and knee flexion angle in walking, hip and knee flexion angle in running or exercising, frequency of head rotation, maximum range of head rotation angle, and frequency of swallowing. Again, it is understood that these physical activities are merely exemplary only, and additional or different behaviors may be included in the feature vector. Further, the feature vector may include hemodynamic and biomechanical characteristics of healthy patient groups and clinical event patients. Such hemodynamic characteristics may include the pulsatile forces acting on the stent due to the fluid pressure and mechanical forces (e.g., radial compression, bending, torsion, axial tension/compression, etc.). Additionally, the hemodynamic characteristics may include distensibility of arteries and may be measured by ultrasound.

The training phase may further include associating the received one or more variables of the patient's characteristics pertaining to the range and/or frequency of a patient's hip and knee flexion and/or head rotation of as determined in step 323, and the patient's computed mechanical/hemodynamic characteristics as determined in steps 325 and 327 with a clinical events and storing the relationship electronically (e.g., via an electronic storage medium, RAM, etc.). For example, this relationship may be stored in an electronic storage medium of the server systems 106. Further, the training phase may include training a machine learning algorithm (e.g., a linear Support Vector Machine) to analyze and recognize patterns of clinical events from the feature vectors obtained, as described above. Additionally, the training phase may comprise saving the results of the machine learning algorithm as a digital representation. This digital representation may be a memory or digital storage (e.g., a hard drive and/or network drive) of a computational device such as a computer, laptop, DSP, server, etc.

The prediction phase of step 329 may include creating a feature vector of a patient's sedentary behavioral characteristics, physical activity characteristics, and/or hemodynamic characteristics. The feature vector may have the same values and/or quantities as those used in the training phase, as discussed above. Additionally, using the saved results of the machine learning algorithm produced in the training phase (e.g., feature weights), the prediction phase may include producing estimates and/or predictions of the probability of clinical events. These estimates and/or predictions may be produced by the same machine learning technique used in the training phase, described above. Additionally, these estimates and/or predictions of clinical events may be saved to a digital representation or digital storage (e.g., a hard drive and/or network drive) of a computational device such as a computer, laptop, DSP, server, etc. In one embodiment, step 331 may include outputting, e.g., to an electronic storage medium, the estimates and/or predictions of step 329 for use by one or more healthcare providers.

In one embodiment, the training and prediction phases may include feature vectors of both sedentary behavior and physical activity may be incorporated into generating a computational anatomic model of the musculoskeletal and arterial systems of the patient. For example, the system may receive both sedentary (e.g., length/frequency of sitting down, and length/frequency of laying down), as well as activity (number of steps, hip and knee flexion angle in walking, hip and knee flexion angle in running or exercising, etc.) in performing computational fluid dynamics analysis and/or structural mechanics simulation. Thus, the determining the effect of mechanical, hemodynamic, and/or pathological characteristics of the computational anatomic model on clinical events, such as, for example, stent fractures, dissection, plaque rupture, etc., based not only on sedentary behaviors or activity behaviors, but also or alternatively on both sedentary and activity behaviors or characteristics.

Other embodiments of the disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A computer-implemented method of non-invasively assessing a risk of a clinical event in a patient, the method comprising:

obtaining, via an imaging device, one or more images of a patient's anatomy;

generating a first three-dimensional patient-specific vascular model of the patient's anatomy based on the one or more images, including at least one vessel of the patient;

measuring a range of movement and/or frequency of musculoskeletal behavior of the patient while the patient moves via a device associated with the patient;

generating an updated three-dimensional patient-specific vascular model of the patient's anatomy by simulating or detecting a given movement corresponding to the measured range of movement and/or frequency of musculoskeletal behavior of the patient;

computing mechanical and/or hemodynamic characteristics of the patient's vascular system by performing at least one of a computational fluid dynamics analysis or a structural mechanics simulation using the updated three-dimensional patient-specific vascular model;

using the at least one of the computational fluid dynamics analysis or structural mechanics simulation, determining one or more features of the musculoskeletal behavior of the patient while the patient performs the given movement, the one or more features being used to estimate and output an effect of the computed mechanical and/or hemodynamic characteristics on at least one of the patient's risk of disease, a risk of failure of a device, or a performance characteristic of a device;

assessing a risk of a clinical event in the patient based on the given movement, using the estimated effect of the mechanical and/or hemodynamic characteristics of the vascular system of the patient on the at least one of the patient's risk of disease, the risk of failure of a device, or the performance characteristic of a device; and outputting the risk of the clinical event to an electronic storage medium or a display for use by one or more healthcare providers.

2. The computer-implemented method of claim 1, wherein generating the updated three-dimensional patient-specific vascular model of the patient's anatomy comprises generating a computational anatomic vascular model of the patient's anatomy.

3. The computer-implemented method of claim 2, wherein the updated three-dimensional patient-specific vascular model of the patient's anatomy is generated using images of the patient's venous system in various postures taken by a magnetic resonance imaging (MRI) system.

4. The computer-implemented method of claim 1, wherein the musculoskeletal behavior of the patient includes a head rotation.

5. The computer-implemented method of claim 1, wherein estimating the effect of the mechanical and/or hemodynamic characteristics of the vascular system of the patient on at least one of the patient's risk of disease, the risk of failure of a device, or the performance characteristic of a device includes executing one or more learned algorithms.

6. The computer-implemented method of claim 5, wherein executing the one or more learned algorithms comprises a training phase and a prediction phase.

7. The computer-implemented method of claim 6, wherein the training phase includes creating a feature vector of healthy patients and patients suffering from known clinical events or disease.

8. The computer-implemented method of claim 7, wherein the musculoskeletal behavior of the patient includes a head rotation.

9. A computer system for non-invasively assessing a risk of a clinical event in a patient, the system comprising:

at least one data storage device storing instructions for determining an effect of musculoskeletal activities in diagnosing or treating disease; and at least one processor configured to execute the instructions to perform operations comprising:

obtaining, via an imaging device, one or more images of a patient's anatomy;

generating a first three-dimensional patient-specific vascular model of the patient's anatomy based on the one or more images, including at least one vessel of the patient;

measuring a range of movement and/or frequency of musculoskeletal behavior of the patient while the patient moves via a device associated with the patient;

generating an updated three-dimensional patient-specific vascular model of the patient's anatomy by simulating or detecting a given movement corresponding to the measured range of movement and/or frequency of musculoskeletal behavior of the patient;

computing mechanical and/or hemodynamic characteristics of the patient's vascular system at a given posture by performing at least one of a computational fluid dynamics analysis or a structural mechanics simulation using the updated three-dimensional patient-specific vascular model;

using the at least one of the computational fluid dynamics analysis or structural mechanics simulation, determining one or more features of the musculoskeletal behavior of the patient while the patient performs the given movement, the one or more features being used to estimate and output an effect of the computed mechanical and/or hemodynamic characteristics on at least one of the patient's risk of disease, a risk of failure of a device, or a performance characteristic of a device;

assessing a risk of a clinical event in the patient at the given posture, using the estimated effect of the mechanical and/or hemodynamic characteristics of the vascular system of the patient on the at least one of the patient's risk of disease, the risk of failure of a device, or the performance characteristic of a device; and outputting the risk of the clinical event to an electronic storage medium or a display for use by one or more healthcare providers.

10. The system of claim 9, wherein generating the updated three-dimensional vascular model of the patient's anatomy further comprises generating a computational anatomic vascular model of the patient's anatomy.

11. The system of claim 10, wherein the updated three-dimensional patient-specific vascular model of the patient's anatomy is generated using images of the patient's venous system in various postures taken by a magnetic resonance imaging (MRI) system.

12. The system of claim 10, wherein the musculoskeletal behavior of the patient a head rotation.

13. The system of claim 9, wherein estimating the effect of the mechanical and/or hemodynamic characteristics of the vascular system of the patient on at least one of the patient's risk of disease, the risk of failure of a device, or the performance characteristic of a device includes executing one or more learned algorithms.

14. The system of claim 13, wherein executing the one or more learned algorithms comprises a training phase and a prediction phase.

15. The system of claim 14, wherein the training phase includes creating a feature vector of healthy patients and patients suffering from known clinical events or disease.

16. The system of claim 15, wherein the musculoskeletal behavior of the patient includes a head rotation.

17. A non-transitory computer readable medium storing computer-executable programming instructions for performing a method of non-invasively assessing a risk of a clinical event in a patient, the method comprising:
- obtaining, via an imaging device, one or more images of a patient's anatomy;
- generating a first three-dimensional patient-specific vascular model of the patient's anatomy based on the one or more images, including at least one vessel of the patient;
- measuring a range of movement and/or frequency of musculoskeletal behavior of the patient while the patient moves via a device associated with the patient;
- generating an updated three-dimensional patient-specific vascular model of the patient's anatomy by simulating or detecting a given movement corresponding to the measured range of movement and/or frequency of musculoskeletal behavior of the patient;
- computing mechanical and/or hemodynamic characteristics of the patient's vascular system at the given movement by performing at least one of a computational fluid dynamics analysis or a structural mechanics simulation using the updated three-dimensional patient-specific vascular model;
- using the at least one of the computational fluid dynamics analysis or structural mechanics simulation, determining one or more features of the musculoskeletal behavior of the patient while the patient performs the given movement, the one or more features being used to estimate and output an effect of the computed mechanical and/or hemodynamic characteristics on at least one of the patient's risk of disease, a risk of failure of a device, or a performance characteristic of a device;
- assessing a risk of a clinical event in the patient at the given movement, using the estimated effect of the mechanical and/or hemodynamic characteristics of the vascular system of the patient on the at least one of the patient's risk of disease, the risk of failure of a device, or the performance characteristic of a device; and
- outputting the risk of the clinical event to an electronic storage medium or a display for use by one or more healthcare providers.

18. The non-transitory computer readable medium of claim 17, wherein generating the updated three-dimensional vascular model of the patient's anatomy further comprises generating a computational anatomic vascular model of the patient's anatomy.

19. The non-transitory computer readable medium of claim 17, wherein the updated three-dimensional patient-specific vascular model of the patient's anatomy is generated using images of the patient's venous system in various postures taken by a magnetic resonance imaging (MRI) system.

20. The non-transitory computer readable medium of claim 17, wherein the musculoskeletal behavior of the patient includes a head rotation.

* * * * *